(12) United States Patent
Borders et al.

(10) Patent No.: US 6,832,398 B2
(45) Date of Patent: *Dec. 21, 2004

(54) SURGICAL TABLE

(75) Inventors: Richard L. Borders, Cincinnati, OH (US); David C. Newkirk, Lawrenceburg, IN (US)

(73) Assignee: Hill-Rom Services, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/299,895

(22) Filed: Nov. 19, 2002

(65) Prior Publication Data

US 2003/0061661 A1 Apr. 3, 2003

Related U.S. Application Data

(63) Continuation of application No. 09/592,692, filed on Jun. 13, 2000, now Pat. No. 6,484,334, which is a continuation-in-part of application No. 09/188,785, filed on Nov. 6, 1998, now Pat. No. 6,073,284.
(60) Provisional application No. 60/064,709, filed on Nov. 7, 1997, and provisional application No. 60/101,585, filed on Sep. 24, 1998.

(51) Int. Cl.[7] .................. A61G 13/08; A61G 13/10; A61G 7/00; A47C 27/10
(52) U.S. Cl. .................... 5/600; 5/618; 5/713
(58) Field of Search .................. 5/600, 613, 618, 5/710, 713, 654, 714

(56) References Cited

U.S. PATENT DOCUMENTS

| RE22,763 E | 6/1946 | Clark |
|---|---|---|
| 2,606,996 A | 8/1952 | Westerberg et al. |
| 3,206,188 A | 9/1965 | Douglass, Jr. |
| 3,451,071 A | 6/1969 | Whiteley |
| 3,845,946 A | 11/1974 | Warden et al. |
| 3,868,103 A | 2/1975 | Pageot et al. |
| 4,127,906 A | 12/1978 | Zur |
| 4,195,829 A | 4/1980 | Reser |
| 4,394,784 A | * 7/1983 | Swenson et al. |
| 4,761,000 A | 8/1988 | Fisher et al. |
| 5,103,519 A | 4/1992 | Hasty |
| 5,121,512 A | 6/1992 | Kaufmann |

(List continued on next page.)

FOREIGN PATENT DOCUMENTS

| CH | 678 390 | 9/1991 |
|---|---|---|
| DE | 0 200 823 | 7/1973 |
| DE | 39 01 336 | 7/1989 |
| DE | 195 34 956 | 3/1997 |
| DE | 200 03 700 | 6/2000 |
| EP | 0 292 218 | 11/1988 |
| EP | 0 821 928 | 2/1998 |
| FR | 2 391 716 | 12/1978 |
| FR | 2 435 245 | 4/1980 |
| FR | 2 648 706 | 12/1990 |
| WO | WO 87/06209 | 10/1987 |
| WO | WO 97/12531 | 4/1997 |
| WO | WO 99/07320 | 2/1999 |
| WO | WO 99/23992 | 5/1999 |

OTHER PUBLICATIONS

US 5,813,067, 9/1998, Stacy et al. (withdrawn)

Primary Examiner—Alexander Grosz
(74) Attorney, Agent, or Firm—Bose McKinney & Evans LLP

(57) ABSTRACT

A support apparatus includes a base, a frame coupled to the base, and a mattress supported by the frame. The apparatus also includes a coupler for coupling a power pack to one of the base, the frame and the mattress. The power pack is pivotable between a first area substantially underneath the frame and a second area substantially outside the first area.

21 Claims, 14 Drawing Sheets

U.S. PATENT DOCUMENTS

| | | |
|---|---|---|
| 5,181,288 A | 1/1993 | Heaton et al. |
| 5,208,928 A | 5/1993 | Kuck et al. |
| 5,235,713 A | 8/1993 | Guthrie et al. |
| 5,251,347 A | 10/1993 | Hopper et al. |
| 5,291,959 A | 3/1994 | Malblanc |
| 5,394,577 A | 3/1995 | James et al. |
| 5,444,878 A | 8/1995 | Kang |
| 5,505,518 A | 4/1996 | Pike |
| 5,528,782 A | 6/1996 | Pfeuffer et al. |
| 5,556,169 A | 9/1996 | Parrish et al. |
| 5,564,662 A | 10/1996 | Lussi et al. |
| 5,623,736 A | 4/1997 | Soltani et al. |
| 5,647,079 A | 7/1997 | Hakamiun et al. |
| 5,687,438 A | 11/1997 | Biggie et al. |
| 5,699,570 A * | 12/1997 | Wilkinson et al. |
| 5,701,622 A | 12/1997 | Biggie et al. |
| 5,702,536 A | 12/1997 | Carruth |
| 5,754,997 A | 5/1998 | Lussi et al. |
| 5,774,915 A | 7/1998 | Scott et al. |
| 5,881,410 A | 3/1999 | Yamada |
| 5,966,763 A | 10/1999 | Thomas et al. |

* cited by examiner

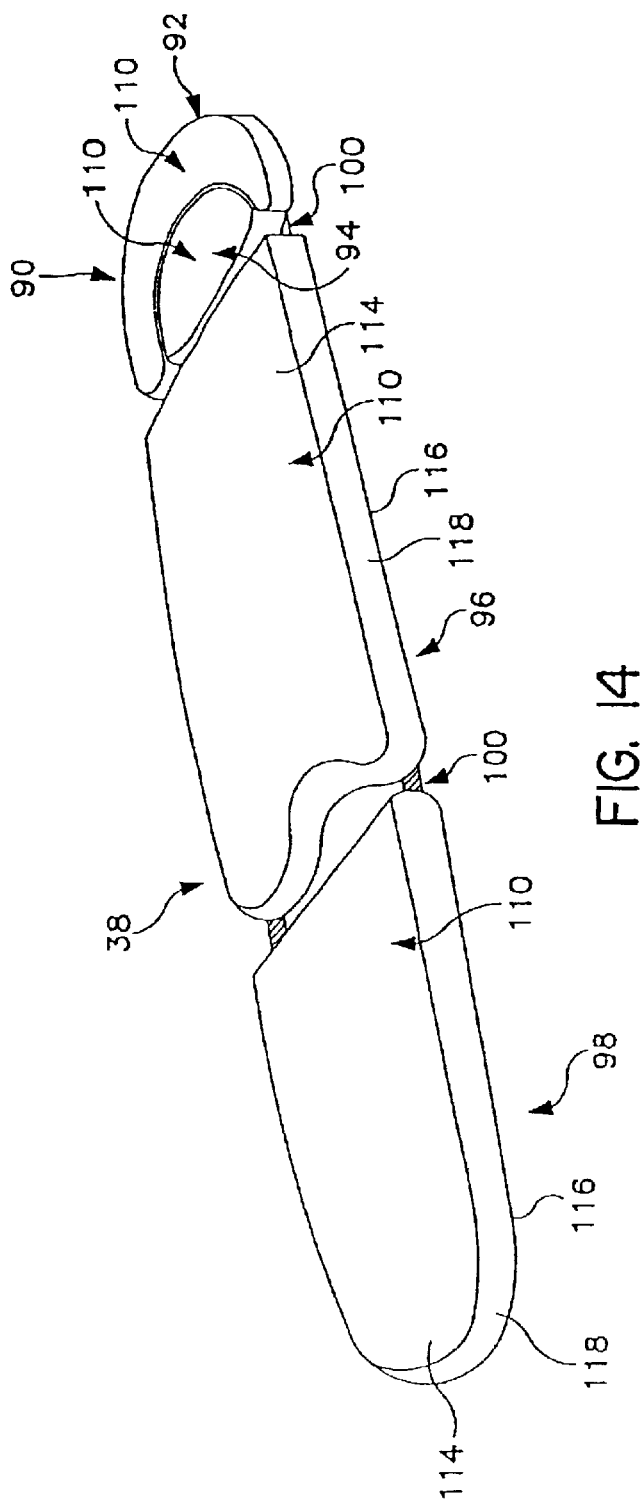
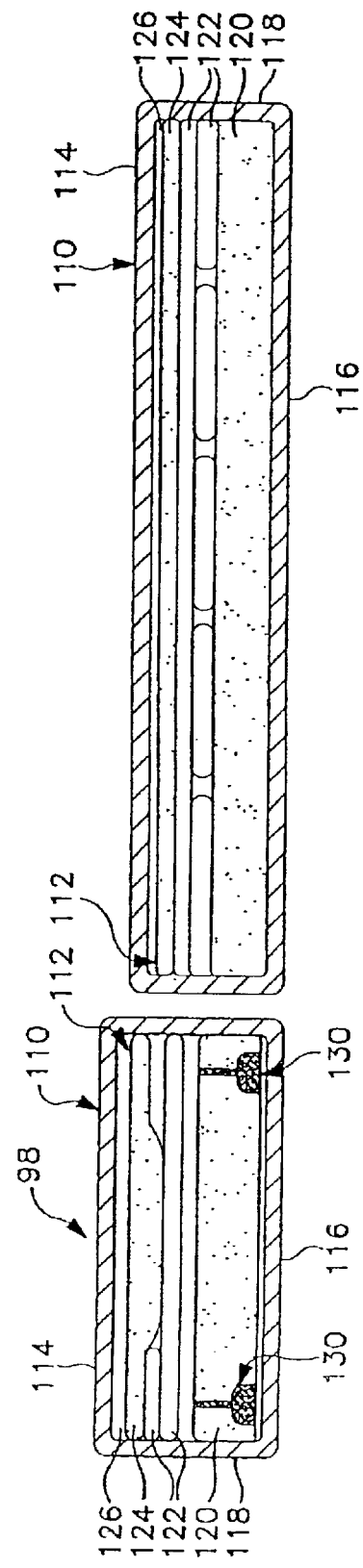

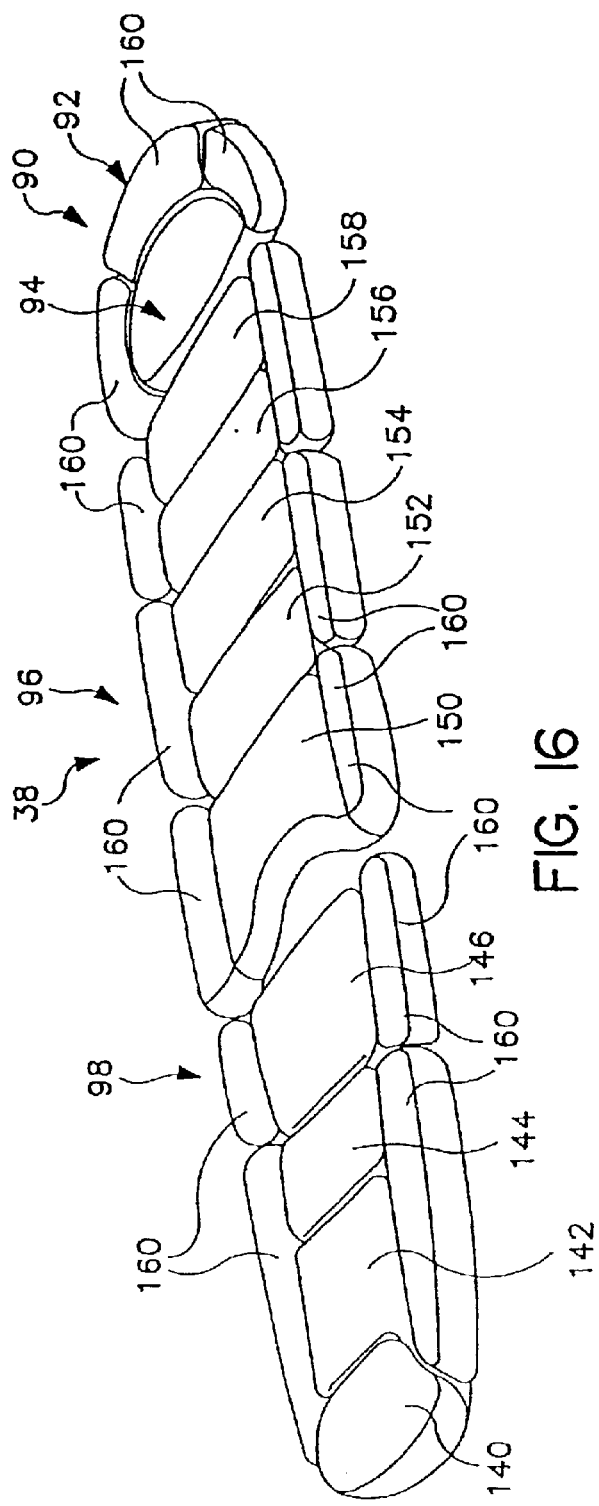
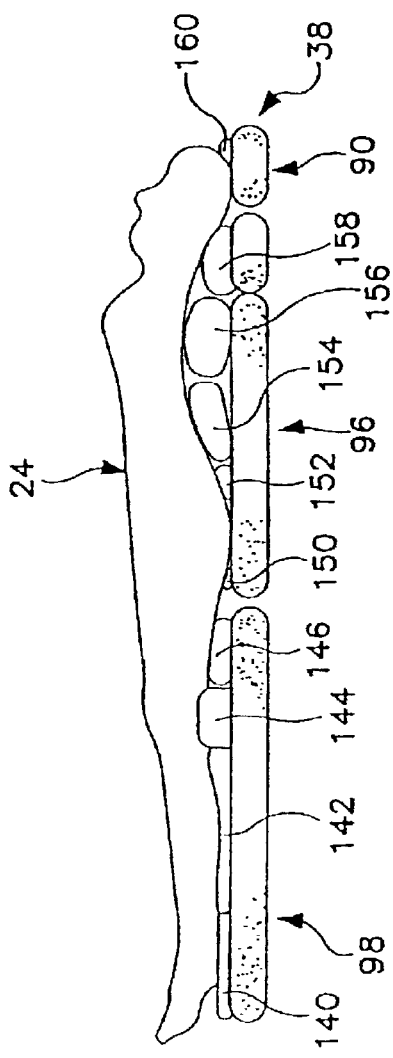
FIG. 16
FIG. 17

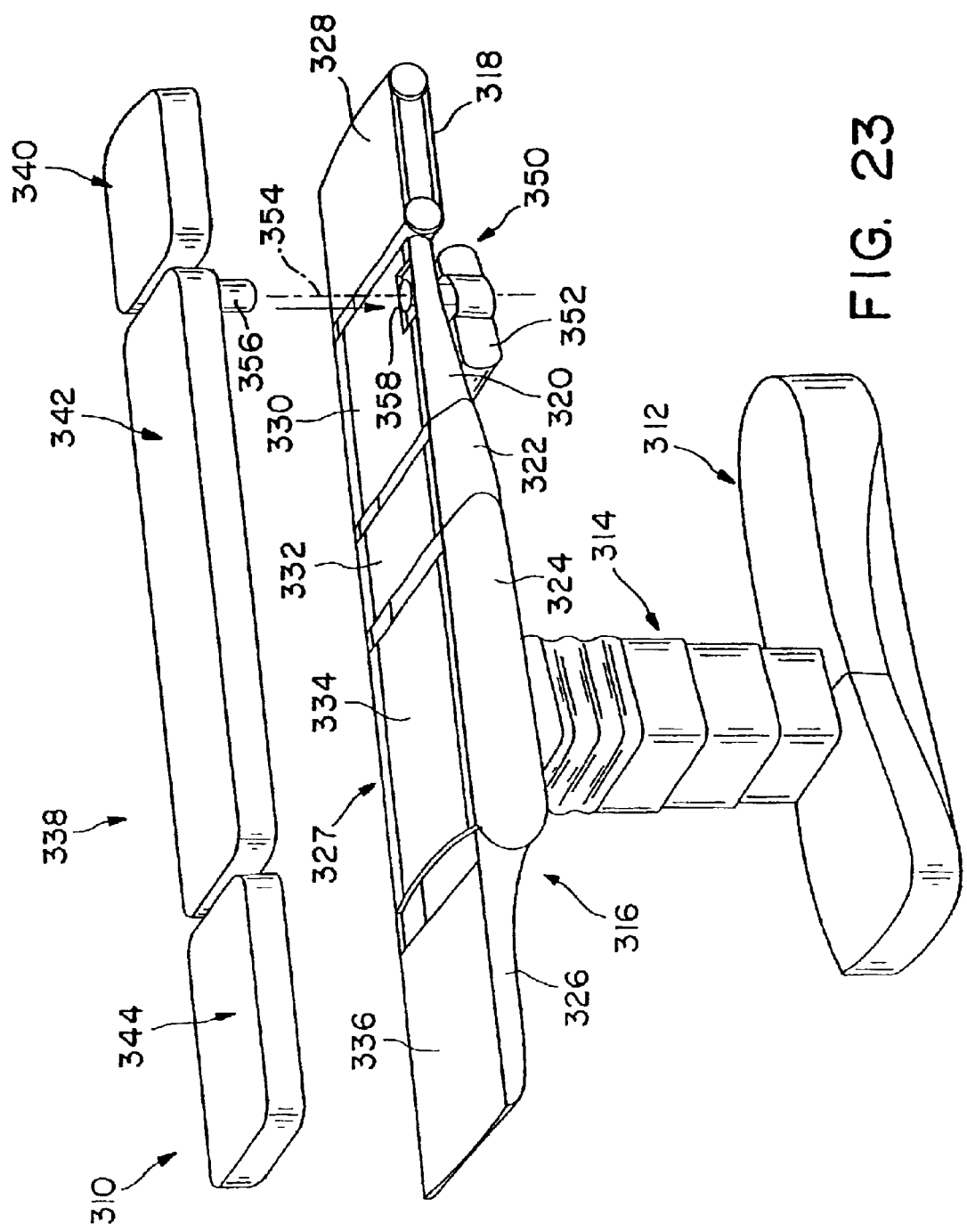

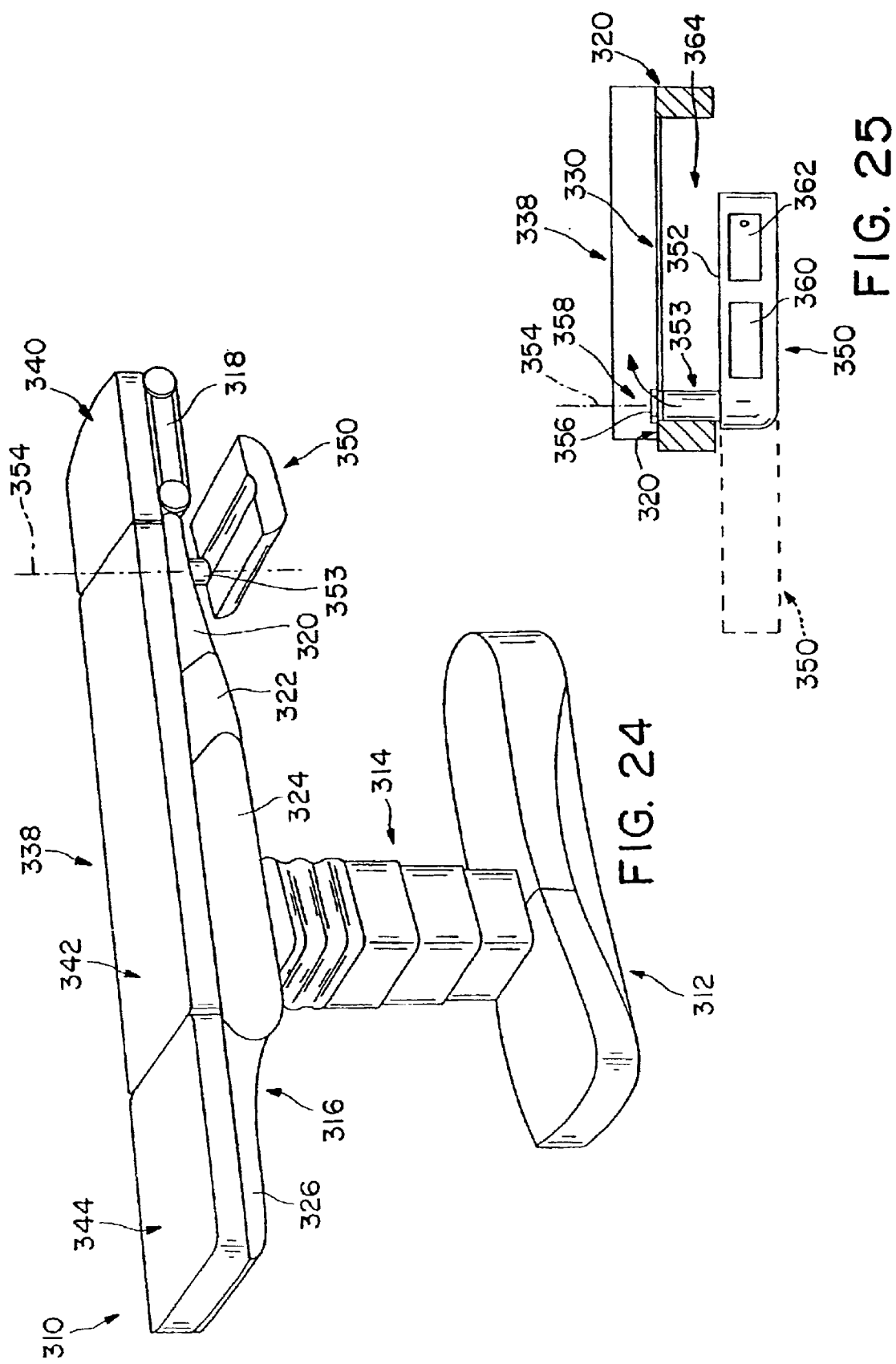

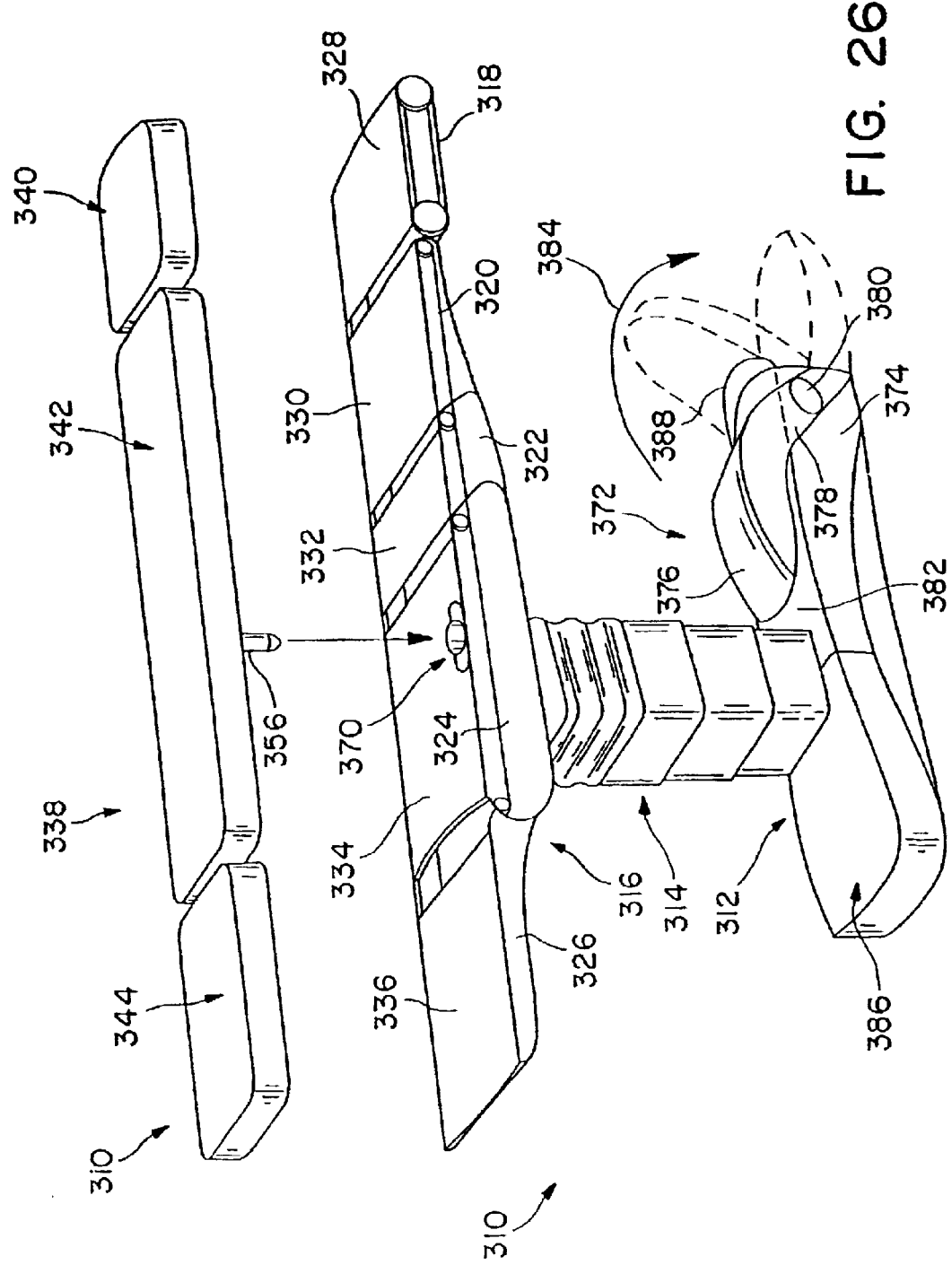

SURGICAL TABLE

This application is a continuation of U.S. application Ser. No. 09/592,692, filed on Jun. 13, 2000, now U.S. Pat. No. 6,484,334, which is a continuation-in-part of U.S. application Ser. No. 09/188,785, filed on Nov. 6, 1998, now U.S. Pat. No. 6,073,284, which claimed the benefit of U.S. Provisional Application Ser. No. 60/064,709 filed Nov. 7, 1997 and U.S. Provisional Application Ser. No. 60/101,585 filed Sep. 24, 1998, the disclosures of which are incorporated herein by reference.

BACKGROUND AND SUMMARY OF THE INVENTION

The present invention relates to an operating room or surgical table. More particularly, the present invention relates to a surgical table including a mattress having a plurality of inflatable bladders for supporting a patient and a power pack configured to supply air to the bladders.

Operating room tables are long known in the health care industry for supporting patients during surgical procedures. In recent years, surgical tables have been made even more useful and convenient for doctors and nurses by adding various features and options, such as powered articulation of head, torso, and leg sections of the surgical table, height adjustment, tilt adjustment, trend adjustment, etc. While these features and options give doctors great flexibility for supporting patients in a variety of positions that are best suited for a given surgical procedure, they also may become more difficult and frustrating to use. In addition, surgical tables having numerous control features often require separate power packs for supplying the necessary power for moving the table to different positions. Furthermore, mattress surface systems have likewise become more technically sophisticated which frequently makes them more cumbersome and frustrating to use.

According to one illustrated embodiment of the present invention, a surgical table includes a base, a vertical support member extending vertically upwardly from the base, a frame extending outwardly from the support member, and a mattress supported by the frame and positioned to lie above the frame. The mattress is configured to support a patient and has at least one bladder configured to receive a medium. The surgical table also includes a power pack positioned to lie within the base and configured to supply the medium to the mattress to change the shape of the mattress.

In one illustrated embodiment, the medium supplied by the power pack to the mattress is air. In another illustrated embodiment, the medium supplied by the power pack to the mattress is a liquid. The power pack is further configured to supply heat to the mattress to change the temperature of the mattress. Illustratively, a flexible hose extends from the power pack to the mattress for delivery of the medium from the power pack to the mattress. The hose is concealed within the base and the vertical support member of the frame.

According to another illustrated embodiment of the present invention, a surgical table includes a base, a frame positioned in spaced-apart relation to the base, and a vertical support member interconnecting the frame and the base. The support member is configured to telescope vertically to position the frame at a variety of different heights relative to the base. The surgical table also includes a mattress positioned to lie above the frame and configured to support a patient. The mattress includes a cover having an upwardly-facing patient-support surface and defining an interior region of the mattress and a plurality of bladders received in the interior region of the cover and configured to be inflatable to position the patient in a predefined surgical position on the mattress. The surgical table further includes a blower positioned to lie within the base of the frame and configured to supply air to the bladders to inflate the bladders.

According to yet another illustrated embodiment of the present invention, a surgical table includes a frame having a patient-support platform and a mattress positioned to lie on the patient-support platform. The mattress is configured to support a patient during a surgical procedure. The mattress includes a cover having an upwardly-facing patient-support surface and defining an interior region of the mattress and a plurality of bladder pairs received in the interior region of the cover and extending laterally across the mattress. The bladder pairs are positioned to lie adjacent to one another and each bladder pair has a bottom bladder and a top bladder positioned to lie above the bottom bladder. Each bladder within each bladder pair is individually inflatable to position the patient in a predefined surgical position on the mattress.

According to a further illustrated embodiment of the present invention, a surgical table includes a mattress, a patient-support platform positioned below the mattress and configured to support the mattress, a base positioned in spaced-apart relation to the patient-support platform, and a vertical support member interconnecting the base and the patient-support platform. The support member is configured to support the patient-support platform at a variety of different heights relative to the base. The surgical table also includes a power pack positioned to lie within the base and configured to supply a medium to the mattress to change the shape of the mattress to position a patient in a predefined surgical position, and a hose interconnecting the power pack and the mattress. The hose is configured to transfer the medium from the power pack to the mattress. The surgical table further includes a controller positioned in close proximity to the power pack. The controller is configured to control the distribution of the medium from the power pack to the mattress to control the shape of the mattress.

Also according to the present invention, a patient support apparatus includes a base, a frame coupled to the base, and a mattress supported by the frame and positioned to lie above the frame to support a patient. The mattress has at least one bladder configured to receive a medium. The apparatus also includes a power pack pivotably coupled to one of the base, the frame and the mattress and configured to supply the medium to the at least one bladder of the mattress.

In one illustrated embodiment, the power pack is pivotably coupled to the frame by a pivot connector. The power pack is configured to supply the medium to the at least one bladder of the mattress through the pivot connector. The illustrated pivot connector includes a receptacle configured to receive an air coupling of the air mattress to supply air from the power pack through the air coupling to the at least one bladder. The power pack is pivotable from a first position in which the power pack is located substantially under the frame to a second position in which the power pack is located substantially outside the frame.

In another illustrated embodiment, the power pack is pivotably coupled to the base. The power pack is pivotable from a first position in which the power pack is located above a top surface of the base and substantially within a footprint of the base to the second position in which the power pack is located substantially outside the footprint of the base.

In yet another illustrated embodiment, the power pack is tethered to the mattress. The mattress includes a tether connector coupled to the mattress and the power pack. The tether connector extends between adjacent deck sections so that the power pack is positioned below the deck sections and the frame when the mattress is located on the deck sections. The power pack is movable relative to the frame and the deck sections to first and second spaced apart storage positions.

Additional features of the present invention will become apparent to those skilled in the art upon consideration of the following detailed description of the presently perceived best mode of carrying out the invention.

BRIEF DESCRIPTION OF THE DRAWINGS

The detailed description particularly refers to the accompanying figures in which:

FIG. 14 is a perspective view of the mattress of FIGS. 9–13 showing the mattress including a leg section, a torso section, and a head section;

FIG. 15a is a side sectional view of the torso section of the mattress of FIG. 14 showing the mattress having a lower foam mattress structure, high amplitude air bladders positioned atop the foam mattress structure, a Styrofoam bead bag position stabilizer positioned atop the high amplitude air bladders, and a thermal pad positioned atop the Styrofoam bead bag position stabilizer;

FIG. 15b is an end sectional view of the torso section of the mattress of FIG. 14 showing the foam mattress structure being formed to include a pair of flow paths to allow a medium to be supplied from a bottom surface of the mattress through the flow paths in the foam mattress structure so that the air bladders can be inflated and/or deflated:

FIG. 16 is a perspective view of the mattress of FIG. 14 showing each section of the mattress having a plurality of different zones that can be individually inflated or deflated;

FIG. 17 is a side elevation view of a patient being positioned atop the mattress of FIGS. 9–16, showing the mattress being used to position the patient in a predefined surgical position;

FIG. 23 is an exploded perspective view illustrating another embodiment of a surgical table of the present invention including a frame supporting an articulating deck, air mattress located on the deck, and a power pack including an air supply for the air mattress pivotably coupled to the frame;

FIG. 24 is a perspective view of the surgical table of FIG. 23 illustrating the air mattress located on the deck and the power pack pivoted outwardly relative to the support frame;

FIG. 25 is a sectional view taken through the frame and deck of FIG. 24 illustrating further details of a connection of the power pack to the frame;

FIG. 26 is a perspective view of another embodiment of the present invention illustrating a patient support frame and deck having air coupling configured to mate with a coupling of an air mattress and a power pack including an air supply for the air mattress and a plurality of valves pivotably coupled to a base of the surgical table;

DETAILED DESCRIPTION OF THE DRAWINGS

Figure 1:
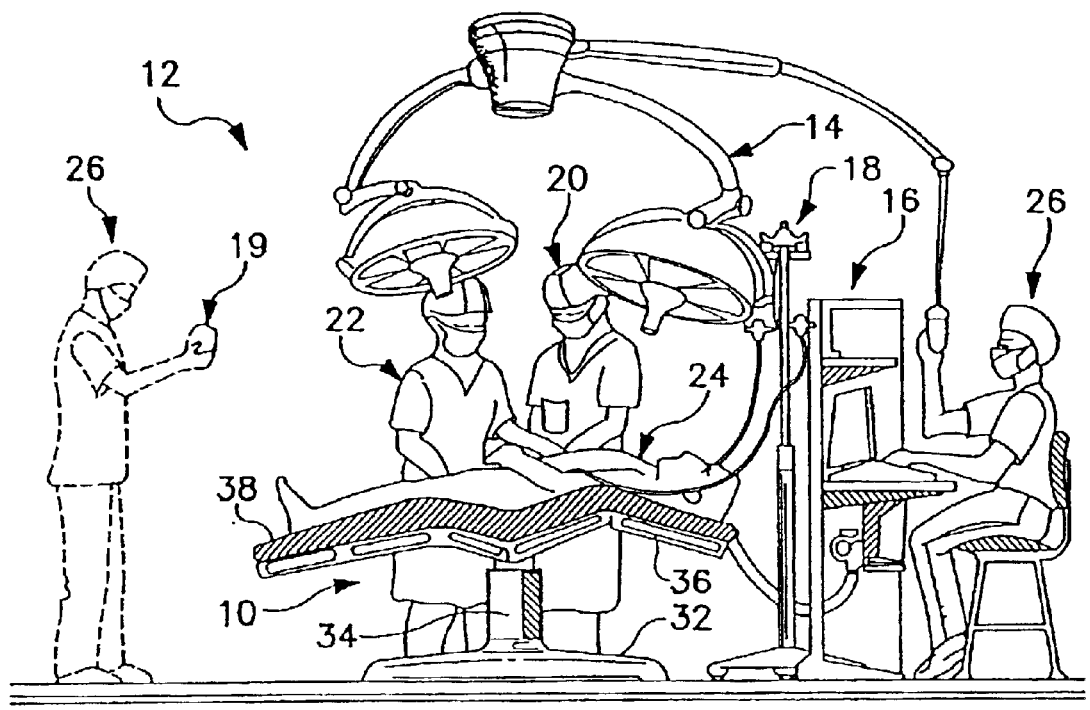
FIG. 1 is a perspective view of a surgical table of the present invention being used in an operating room environment showing a patient lying on the surgical table, a pair of surgeons operating on the patient, a first nurse sitting at a central control station configured to control the lighting, the surgical table, and other operating room equipment, and a second nurse (shown in phantom) holding a remote controller.

Referring now to the drawings, a surgical table 10 according to the present invention is shown in FIG. 1 as it would normally appear in an operating room 12. As shown in FIG. 1, operating room 12 includes surgical table 10, a surgical lighting system 14, a control station 16, an IV stand 18, and a medical device controller 19. As shown in FIG. 1, a surgeon 20 and one or more assistants 22 typically perform a procedure on a patient 24 while another caregiver 26, such as an anesthesiologist or a nurse, controls and monitors operating room equipment, including surgical table 10, from control station 16 or from a remote location using controller 19 (as shown in phantom).

As shown in FIGS. 1–8, surgical table 10 enhances the environment of operating room 12 by preserving space in the operating room 12. As described in detail below, surgical table 10 preserves space by having a base 32 that allows a power pack 64 to be stored within the base 32. Thus, the power pack 64 need not be a separate piece of operating room equipment that takes up additional floor space in operating room 12. Instead, power pack 64 is contained within base 32 of surgical table 10.

As shown in FIGS. 9–22, surgical table 10 also enhances the environment and efficiency of the surgeon 20 working in operating room 12 by having a mattress system 38 that allows the surgeon 20 to position the patient 24 in a predetermined surgical position that corresponds to a particular surgical procedure. Of course, surgical table 10 also includes an articulated frame 30, as discussed below, which also allows patient 24 to be positioned in a predetermined surgical position. However, the positioning of patient 24 by using mattress system 38 is supplemental to using articulated frame 30 which enables the surgeon 20 to fine-tune the positioning of patient 24 to obtain easier access to certain portions of patient 24 during the operation.

Details of another suitable frame for use with base 32 and/or mattress system 38 are disclosed in U.S. Pat. No. 6,202,230, entitled SURGICAL TABLE APPARATUS, which is incorporated herein by reference. Similarly, details of a controller for mattress system 38 and/or power pack 64 are disclosed in U.S. Pat. No. 6,351,678, entitled MEDICAL EQUIPMENT CONTROLLER, which is also incorporated herein by reference.

Figure 2:
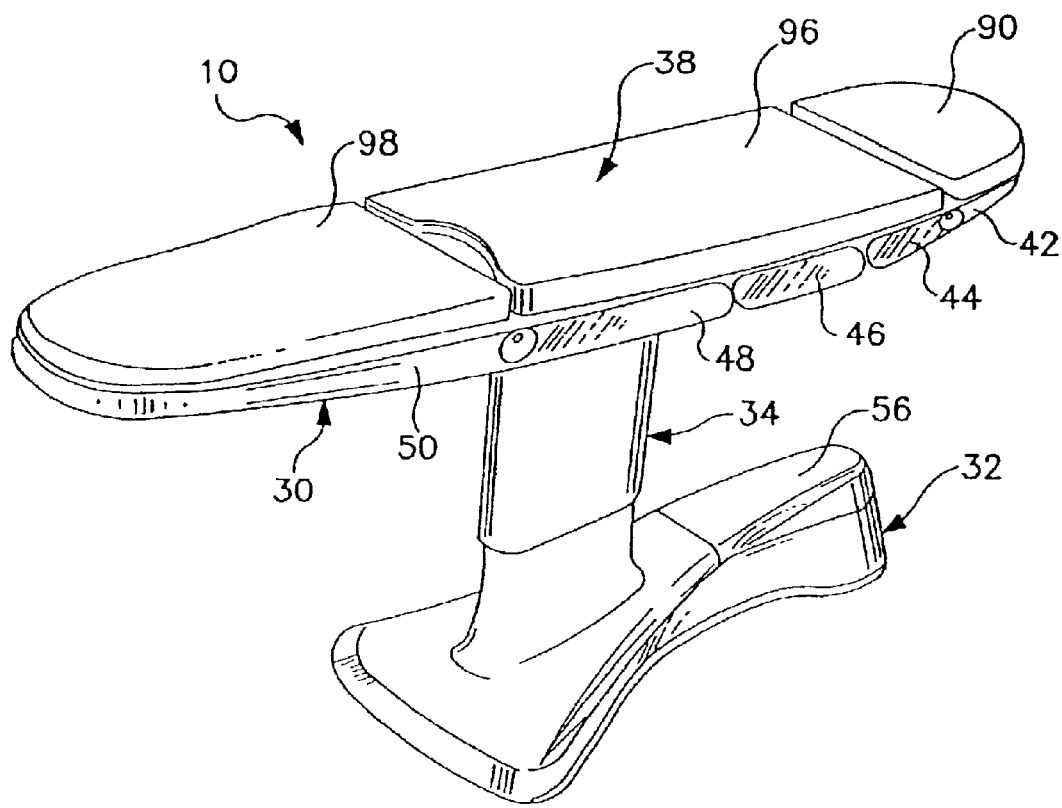
FIG. 2 is a perspective view of the surgical table of FIG. 1 showing the surgical table including a base, a vertical support member (or pedestal) extending upwardly from the base, and an articulated frame extending outwardly from the support member and showing a mattress positioned to lie on the frame and configured to support a patient during a surgical procedure.

As shown in FIGS. 1 and 2, table 10 includes articulated frame 30, base 32, a pedestal 34 interconnecting articulated frame 30 and base 32, and a mattress 38 positioned atop articulated frame 30. Articulated frame 30 includes a head section 42, an upper back section 44, a lower back section 46, a seat section 48, and at least one leg section 50, as shown in FIG. 2. Sections of frame 30 are coupled to longitudinally adjacent sections via pivots so that adjacent sections can be rotated with respect to each other by motors (not shown). Thus, table 10 is configured to receive control signals from control station 16 and/or controller 19 to move sections of articulated frame 30 so that patient 24 can be positioned in a predetermined surgical position as shown in FIG. 1.

Pedestal (or vertical support column) 34 is similarly adjustable to position patient 24 in a predetermined position. Pedestal 34 includes a hi/low mechanism (not shown) for moving the telescoping pedestal 34 upwardly and downwardly to raise and lower the articulated frame 30 relative to the base 32 and the ground. Adjustment of vertical support pedestal 34 can also be controlled by control station 16 and/or controller 19 to position frame surgical table 10 at a predetermined height relative to the ground.

Figure 3:
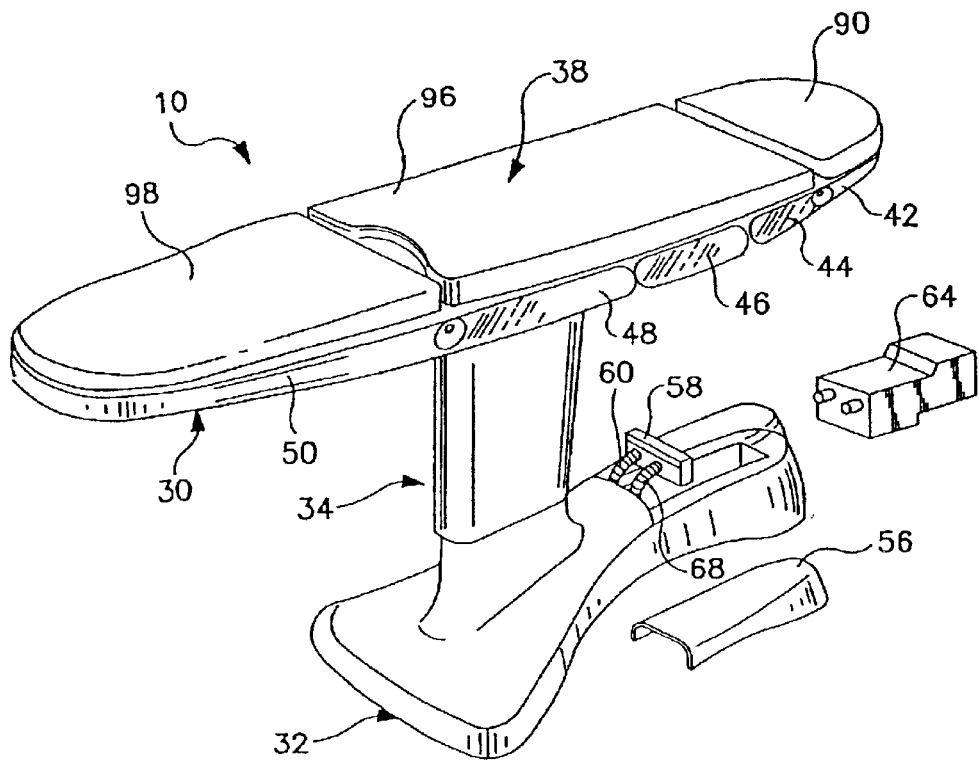
FIG. 3 is a perspective view of the surgical table of FIG. 1 showing the base being formed to include an opening for receiving a power pack.

As shown in FIG. 3, base 32 includes a removable access cover 56 that, when removed, reveals an interior region 66 of base 32. The interior region 66 of base 32 is sized to allow a power pack 64 and a first connector 58 to fit comfortably within the interior region 66 of base 32. Power pack 64 is configured to be coupled to first connector 58 and then located within an interior region 66 of base 32 so that when access cover 56 is reinstalled onto base 32, power pack 64 and connector 58 are concealed within interior region 66 of base 32.

Figure 4:
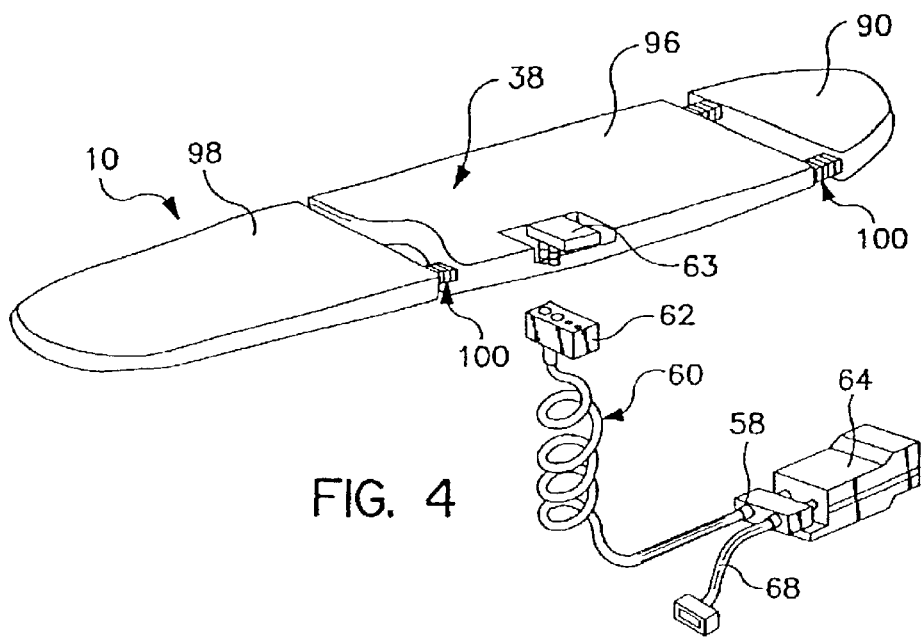
FIG. 4 is a perspective view of the support surface of FIG. 3 with the base and the pedestal removed to show the power pack being plugged into a first connector, a power supply line, and a flexible air/fluid/power handling line (or hose) being coupled to the first connector, the handling line being coiled to extend upwardly through the vertical support member, and a second connector for connecting the second end of the handling line to the mattress.
Figure 5:
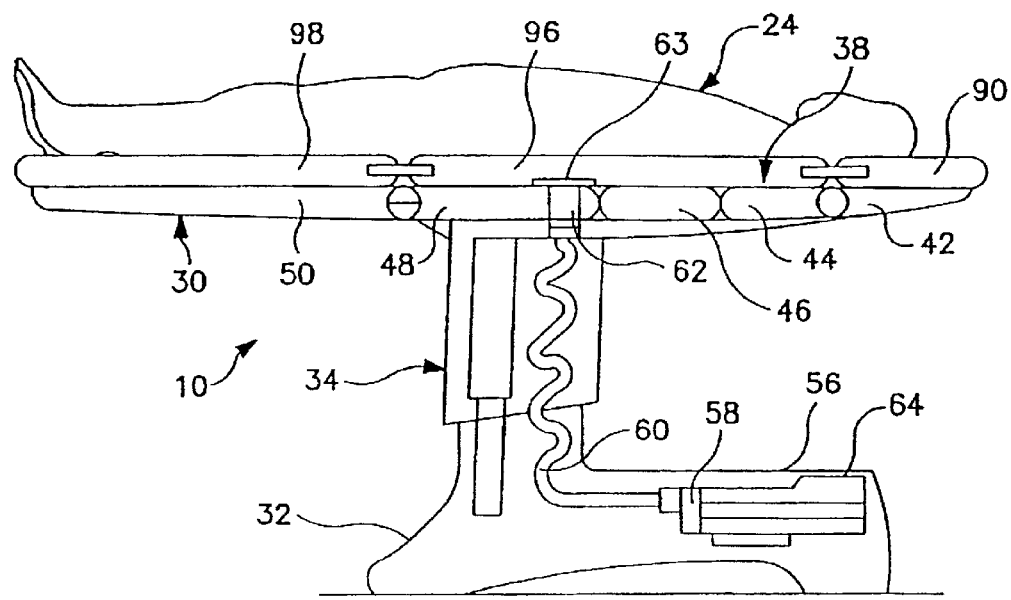
FIG. 5 is a transparent side elevation view of the surgical table of FIGS. 1–4 showing the power pack positioned in the base, the handling line extending through the vertical support member and coupled to the mattress, and a patient positioned atop the mattress.

Power pack 64 is configured to provide power and/or a medium (not shown) to mattress 38 through a delivery line 60, as shown diagrammatically in FIGS. 4 and 5. As shown in FIGS. 4 and 5, a first end of delivery line 60 is coupled to first connector 58 and a second end of delivery line 60 is coupled to a second connector 62. The delivery line 60 extends longitudinally through base 32 and vertically upwardly through pedestal 34 towards mattress 38. The second connector 62 is configured to mate with a third connector 63 integrally coupled to mattress 38. The connectors 58, 62, 63 and delivery line 60 allow power pack 64 to deliver the power and/or medium to mattress 38 in a concealed manner through base 32 and pedestal 34. In other words, all hoses, wiring, pumps, and fluid supply units are completely concealed within the base 38 and telescoping pedestal 34. In addition, in the embodiment of FIGS. 1–5, the power pack 64 is located within a footprint defined by the base 18 and the footprint of the base is sized to be narrower and shorter than a footprint of the frame 30.

Illustratively, power pack 64 includes a controller, a fluid pump, such as a blower, compressor, or liquid pump, and a heating unit for heating the air or fluid. Alternatively, mattress 38 may be supplied with a heating system powered by electricity from power pack 64. The power pack 64 may include battery power or it may be coupled to a wall outlet using a power cord 68, as shown in FIG. 4. Power pack 64 further includes control valves for controlling fluid flow to the various zones of mattress 38 and a processor for controlling operation of the device based on input signals from an operator 26 using control station 16 and/or remote controller 19.

Figure 6:
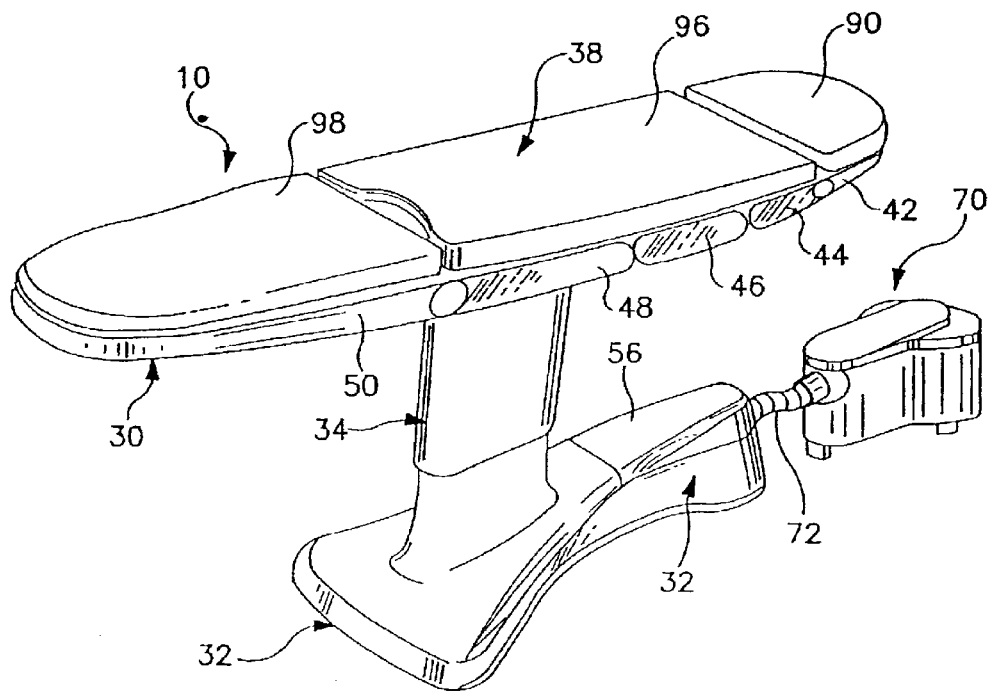
FIG. 6 is a perspective view of a surgical table similar to the surgical tables of FIGS. 1–5, showing the surgical table having a larger power pack external to the base and coupled to the base via an umbilical.
Figure 7:
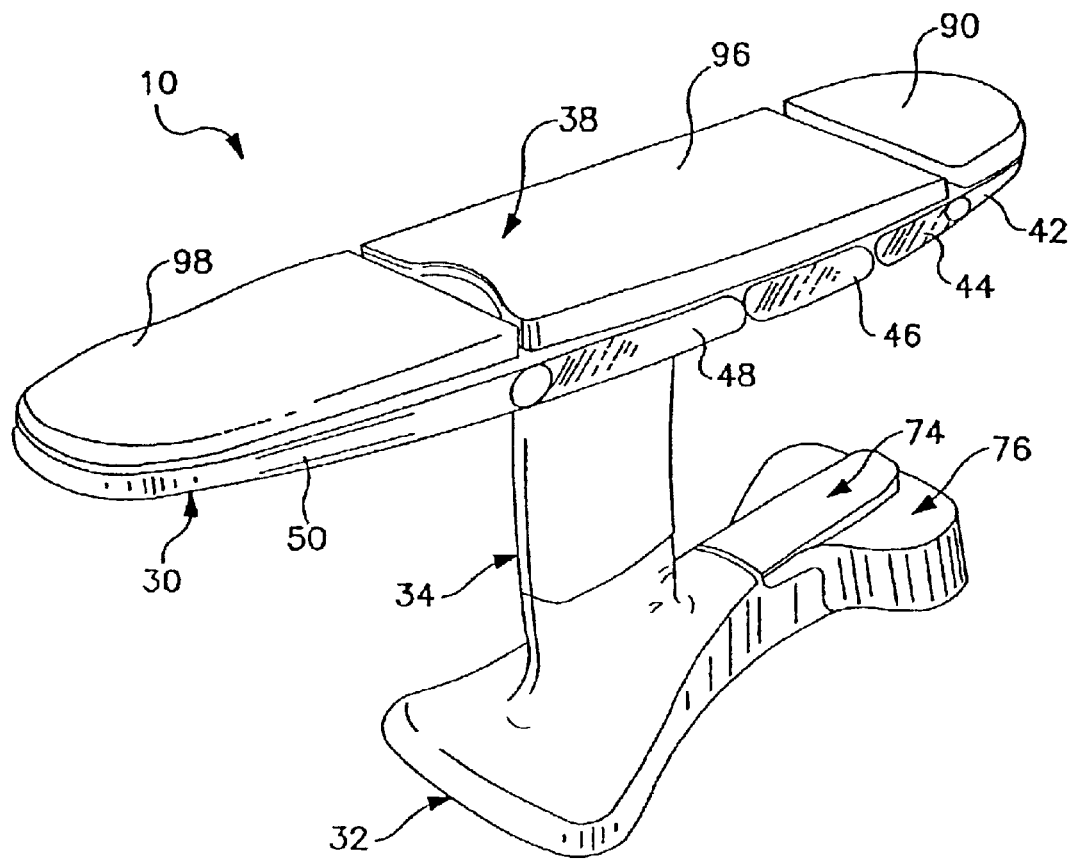
FIG. 7 is a perspective view of a surgical table similar to the surgical tables of FIGS. 1–6, showing the base being formed to be larger to accommodate an even larger power pack.
Figure 8:
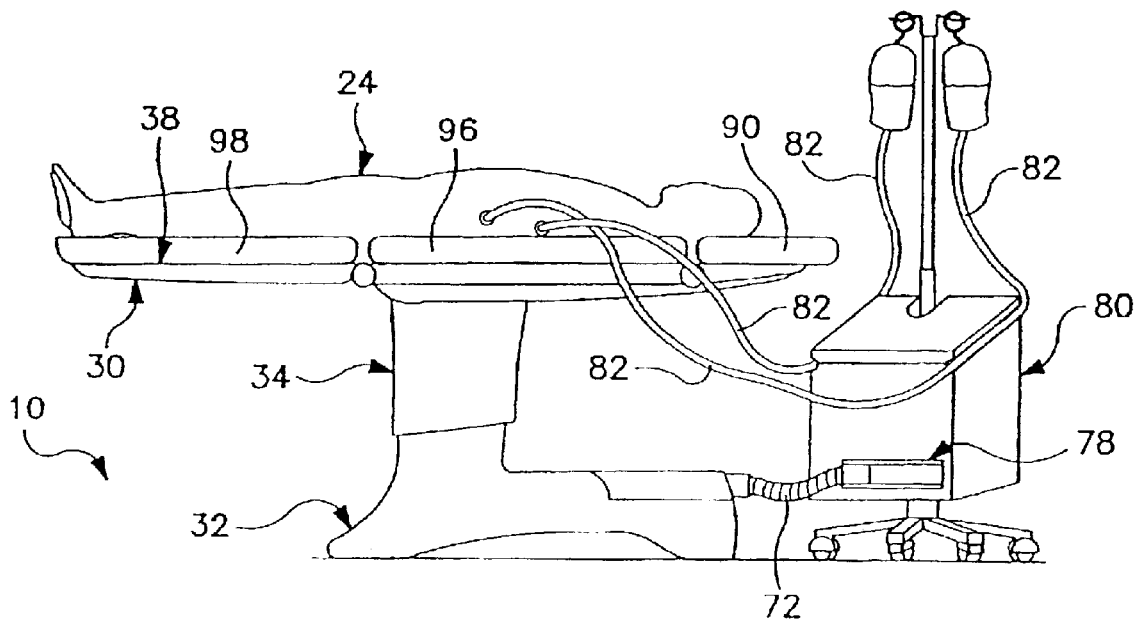
FIG. 8 is a side elevation view of a surgical table similar to the surgical table of FIGS. 1–7, showing an even larger power pack being located on a cart and coupled to the base via an umbilical, the cart including an IV prewarming system so that the patient support and warming needs for surgery are consolidated within the IV prewarming system.

Larger power packs may be required for certain types of mattress systems 38, as shown in FIGS. 6–8. These power packs may be too large to fit into the interior region 66 of base 32 and are therefor positioned external to base 32. FIG. 6 illustrates one example of an external power pack 70 tethered to the base 32 by an umbilical connection 72. The umbilical connection 72 is made at the floor level into the base 32 of the table 10. All other lines and hoses are concealed within the table 10 as discussed above. Power pack 70 may sit on the floor adjacent the table 10. In addition, the power pack 70 may be mounted to an IV pole or stand, or integrated or contained in another piece of equipment such as an anesthesiology machine cart.

An even larger power pack 74 may be integrated with the base 32, as shown in FIG. 7. In this case, a base extension 76 is used to provide a larger footprint that covers a larger area than the original footprint of the base 32. The base extension 76 allows the larger power pack 74 to be coupled to the base 32 at the location where the access cover 56 was originally located.

If an even larger power pack 78 is required, the power pack 78 may be located on a cart 80, as shown in FIG. 8. Again, the power pack 78 is tethered to the base 32 by an umbilical connection 72. In this embodiment, IV lines 82 may be prewarmed by the same cart 80 that contains the power pack 78. This consolidates the patient support and warming needs for surgery in one space-efficient package.

Mattress 38 for use with table 10 is shown in FIGS. 9–22. Mattress 38 allows patient 24 to be positioned in a variety of predetermined surgical positions as shown in FIGS. 9–13. Mattress 38 allows patient 24 to be positioned in a surgical position and/or moved from one surgical position without changing the positioning of articulated frame 30. Thus, mattress 38 acts as an independent patient-positioning device so that various surgical positions can be achieved even for surgical tables having only a flat patient-support platform or for tables having very limited articulation capabilities, such as the patient-support platforms shown in FIGS. 10–13. Mattress 38 also allows the positioning of patient 24 to be fine-tuned when, for example, articulated frame 30 is incapable of the precise positioning required for a particular surgical procedure. Thus, mattress 38 can be used for any surgical table to enhance the patient-positioning capabilities of the particular table.

Figure 9:
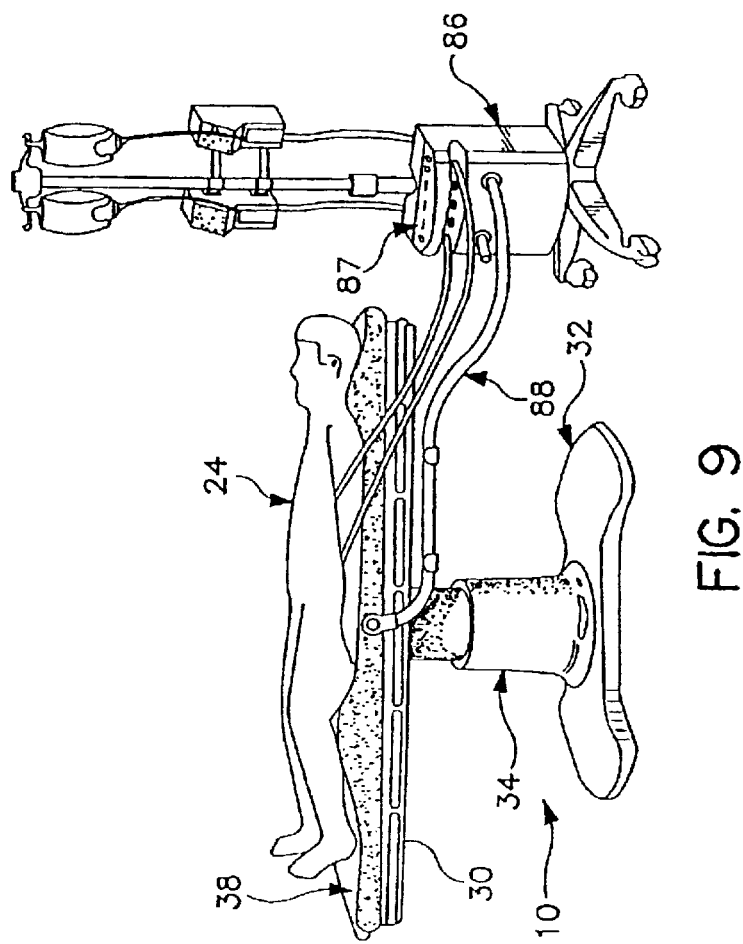
FIG. 9 is a perspective view of a surgical table similar to the surgical tables of FIGS. 1–8, showing the surgical table including a mattress being configured to be inflatable with a liquid or gaseous medium to alter the shape of the mattress so that the patient is positioned in a predefined surgical position.

As shown in FIG. 9, mattress 38 is configured to be coupled to a control apparatus 86 using a tube 88 so that control apparatus 86 can supply a medium (not shown) to mattress 38. The medium supplied by control apparatus 86 to mattress 38 allows mattress 38 to be inflated or deflated to position patient 24 in the desired surgical position. Control apparatus 86 may be controlled by using an input device 87 mounted on control apparatus 86 and/or control station 16 and/or controller 19.

Figure 10:
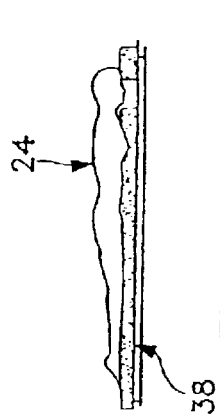
FIGS. 10–13 illustrate a variety of different surgical positions that can be achieved using the mattress and surgical table of FIG. 9.
Figure 11:
Figure 12:
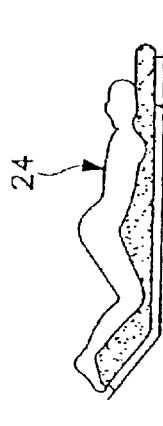
Figure 13:

A variety of different surgical positions can be achieved by inflating or deflating certain portions of mattress 38. For example, as shown in FIG. 9, portions of mattress 38 can be inflated so that mattress 38 pushes upwardly on the back of the knees and back of the neck of patient 24 with the remainder of patient 24 remaining substantially flat on mattress 38. Similarly, as shown in FIG. 10, a portion of mattress 38 can be deflated to allow the face of patient 24 to fit within an opening in mattress 38 created by the deflation of a portion of mattress 38 when patient 24 is lying face down on mattress 38. As shown in FIG. 11, the chest and legs of patient 24 can also be raised by inflating portions of mattress 38. As shown in FIG. 12, a portion of mattress 38 can also be inflated when a leg portion of a surgical table is raised so that the legs of patient 24 are fine-tuned into position while simultaneously inflating and another portion of mattress 24 to raise the posterior of patient 24. In addition, as shown in FIG. 13, a portion of mattress 24 can be inflated to raise the hips of patient 24. Although FIGS. 9–13 illustrate a few examples of the capabilities of mattress 38 for positioning a patient in a predetermined surgical position, it is understood that, as described below, mattress 38 can be used to position a patient in virtually an infinite number of positions.

Mattress 38 is shown in more detail in FIG. 14. As shown in FIG. 14, mattress 38 includes a head section 90, a torso section 96, and a leg section 98. Although not shown in FIGS. 1–13, the head section 90 of mattress 38 may also include an outer head section 92 and an inner head section 94, as shown in FIG. 14. Each section is coupled to its adjacent section using a connector 100, as shown in FIGS. 4 and 14, to allow the medium supplied by control apparatus 86 to be transmitted to the appropriate section of mattress 38.

As shown in FIGS. 14 and 15, each section of mattress 38 includes an outer cover 110 defining an interior region 112 of the respective section. The outer cover 110 of each section of mattress 38 includes a top surface 114, a bottom surface 116, and a perimeter surface 118 interconnecting the top and bottom surfaces 114, 116. The top surface 114 of outer cover 110 is configured to provide a patient-support platform for receiving patient 24. The bottom surface 116 of outer cover 110 is configured to lie on frame 30.

Each portion of mattress 38 also includes a foam mattress structure 120, a plurality of air bladders 122, a bead bag position stabilizer 124, and a thermal pad 126 configured to lie within the interior region 112 of the respective section of mattress 38, as shown in FIG. 15. Foam mattress structure 120 is positioned adjacent to the bottom surface 116 of outer cover 110 so that air bladders 122 can be positioned above foam mattress structure 120 within interior region 112 of outer cover 110. As shown in FIG. 15b, foam mattress structure 120 is formed to include a pair of flow paths 130 to allow the medium supplied by control apparatus 86 to pass through foam mattress structure 120 to air bladders 122. Illustratively, foam mattress structure 120 is made from a Styrofoam material, although a wide variety of different materials may also be used.

Air bladders 122 are illustratively positioned on top of foam mattress structure 120 and extend transversely across mattress 38, as shown in FIGS. 14 and 15. As described below, air bladders 122 are configured to be inflated and/or deflated by the medium supplied by control apparatus 86 to position patient 24 in a desired surgical position.

Bead bag position stabilizer 124 is positioned above air bladders 122 and is configured to freeze the air bladders 122 in the desired surgical position. Details of a suitable bead bag position stabilizer and suitable air bladders for use with mattress system 38 are disclosed in U.S. Pat. No. 5,966,763, which is incorporated herein by reference.

Thermal pad 126 is positioned above air bladders 122 so that thermal pad 126 is positioned adjacent to top surface 114 of outer cover 110. Thermal pad 126 is configured to provide heat to patient 24 lying on top of mattress 38. Thermal pad 126 can be any type of heating device that provides heat to patient 24. Illustratively, thermal pad 126 is made from a conductive thermal material (such as Gorix™) which provides uniform heat across the material when low-voltage electricity is supplied to the material.

As shown in FIGS. 16 and 17, each section of mattress 38 can be formed to include a plurality of zones to provide better patient-positioning control for mattress 38. Illustratively, as shown in FIG. 16, leg section 98 of mattress 38 may be formed to include a foot zone 140, a calf zone 142, a knee zone 144, and a thigh zone 146. Torso section 96 of mattress 38 may be formed to include a seat zone 150, a lower lumbar zone 152, an upper lumbar zone 154, a lower back zone 156, and an upper back zone 158. In addition head section 90, torso section 96, and leg section 98 may each be formed to include a plurality of lateral zones 160. As shown in FIG. 17, by using various zones to position patient 24 on surgical table 10, patient 24 can be positioned in a variety of positions to allow greater flexibility to surgeons to fine-tune the positioning of the patient 24.

Figure 18:
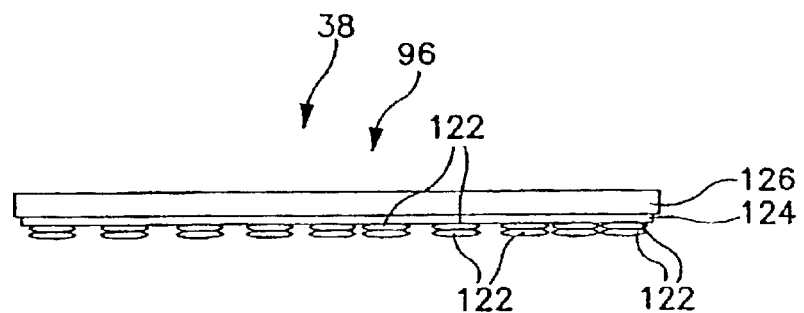
FIG. 18 is a side view of the air bladders of FIG. 15 in a deflated state so that the mattress is substantially flat.
Figure 19:
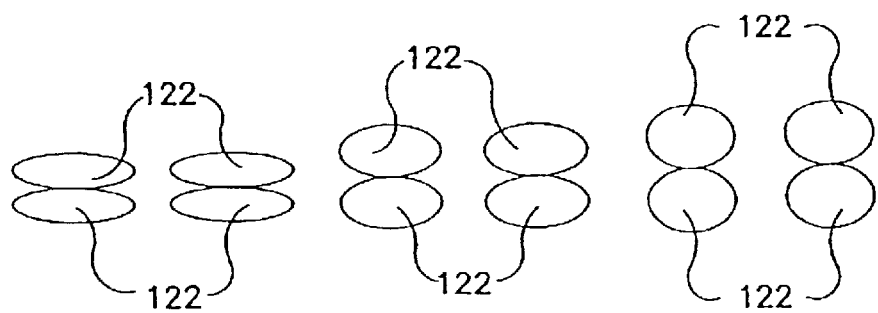
FIG. 19 illustrates the air bladders of FIG. 15 being inflated to change the position of a patient lying atop the mattress.
Figure 20:
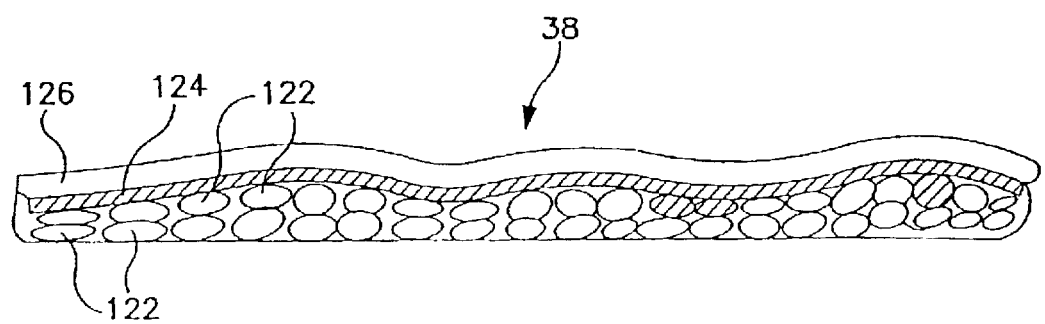
FIG. 20 is a side view of the mattress of FIGS. 9–17, illustrating the mattress conforming to a predetermined shape based on the individual bladders being inflated to certain pressures.

Air bladders 122 are shown in more detail in FIGS. 18–20. As shown in FIGS. 18–20, air bladders 122 are preferably positioned in pairs so that, in the bladder pair, one air bladder is positioned to lie below the other bladder. Each bladder pair is positioned next to another bladder pair within the interior region 112 of outer cover 110 so that each bladder pair abuts another bladder pair within outer cover 110 and the bladder pairs on the ends of the respective section of mattress 38 abut the perimeter surface 188 of outer cover 110. Bladders 122 are preferably configured to extend transversely across mattress 38 so that patient 24 can be positioned as shown in FIG. 17. However, bladders 122 can be configured to extend longitudinally across mattress 38 or in a variety of other positions relative to mattress 38.

As shown in FIG. 19, the shape of bladders 122 change as medium from control apparatus 86 is supplied to the bladders 122. For example, the bladders 122 shown in FIG. 18 and on the left side of FIG. 19 are bladders that have not been supplied with a medium (such as air or liquid) so that these bladders 122 are flat and uninflated. However, moving from left to right in FIG. 19 shows bladders 122 that are progressively more inflated with the medium. Thus, bladders 122 on the far right side of FIG. 19 are fully inflated, while bladders in the middle of FIG. 19 are only partially inflated. As shown in FIG. 19, both air bladders 122 in a given bladder pair are inflated at the same time using the same air-supply line. This allows both bladders 122 within the bladder pair to be similarly sized and shaped before, during, and after the inflating/deflating process.

As shown in FIG. 20, bladders 122 in each section of mattress 38 can be used to adjust the shape of mattress 38 even if the section of mattress 38 does not include separate zones. Although bladders 122 are described herein as air bladders, it is understood that any bladder configured to receive a medium (liquid, solid, or gas) to change the shape of the mattress can be used. In addition, although bladders 122 are shown to be circular in shape, it is understood that any shape bladder, including oval, rectangular, square, triangle, etc., may be used.

Figure 21:
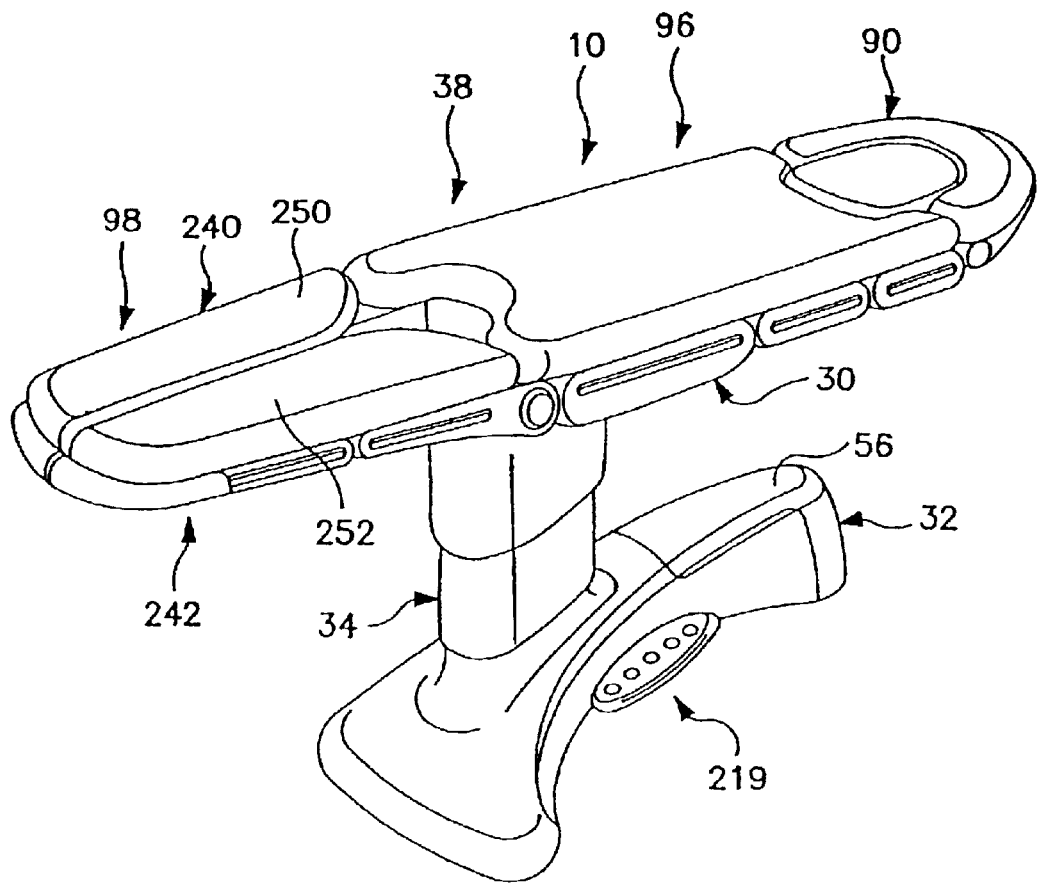
FIG. 21 is a perspective view of the surgical table of FIGS. 1–20, showing the articulated deck panel and mattress each being formed to include a separate leg section for each leg of the patient and showing the base having foot controls for vertically adjusting the deck panel of the surgical table and/or articulating various portions of the deck panel and/or inflating various portions of the bladders to position the patient in a surgical procedure position.
Figure 22:
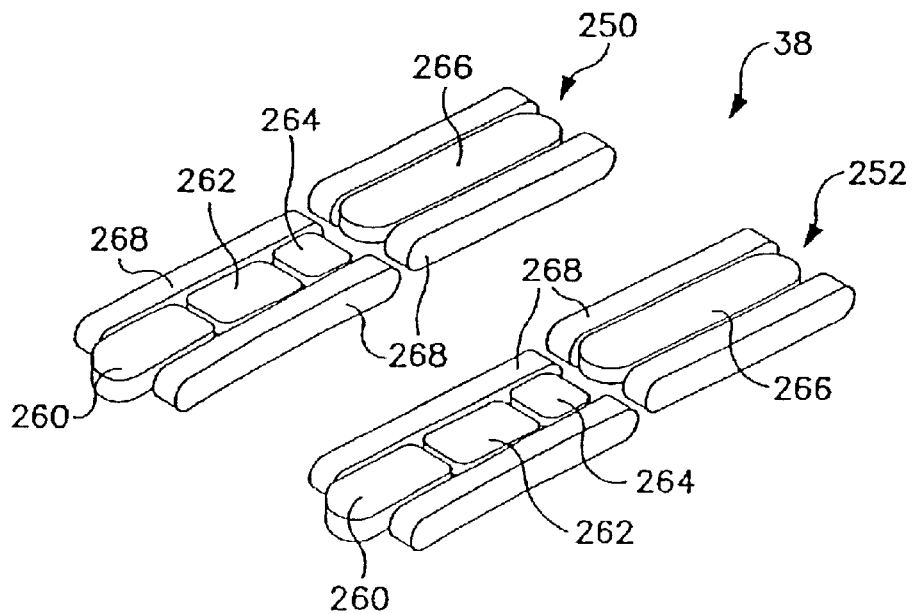
FIG. 22 is a perspective view of leg sections similar to the leg sections of FIG. 21 showing each leg section having multiple zones.

As shown in FIGS. 21 and 22, leg section 50 of frame 30 of surgical table 10 may include a first leg section 240 and a second leg section 242. First and second leg sections 240, 242 allow each leg of patient 24 to be individually positioned. When this type of configuration is used, leg section 98 of mattress 38 is also formed to include a first leg section 250 and a second leg section 252. Each leg section 250, 252 illustratively includes a foot zone 260, an calf zone 262, a knee zone 264, a thigh zone 266, and a plurality of lateral zones 268, as shown in FIG. 22. These zones are configured to operate identically to the zones described above to allow a greater range of positioning of patient 24.

In addition, as shown in FIG. 21, table 10 may include a foot controller 219 mounted to base 32 of table 10. Foot controller 219 is configured to perform the same functions as control station 16 and/or controller 19, except that foot controller 219 is mounted to the base 32 of surgical table 10 so that a surgeon 20 can control the positioning of table 10 and mattress 38 using foot controller 219.

In operation, surgical positioning surface (or mattress) 38 is used as follows. First, the frame 30 and/or pedestal 34 of surgical table 10 is adjusted using control station 16, controller 19, and/or foot controller 219 to place patient 24 in the best possible position. Controller 16, 19, and/or 219 are then used to adjust mattress 38 to fine-tune the positioning of patient 24 on mattress 38. Illustratively, controllers 16, 19, 219 are configured to allow mattress 38 to be automatically adjusted so that air bladders 122 are filled with the medium to fill in the natural gaps between patient 24 and outer cover 110 of mattress 38. Controllers 16, 19, 219 are also configured to allow mattress 38 to be manually adjusted so that each individual bladder pair can be inflated or deflated to enhance the position of patient 24 to improve surgical exposure or access to a particular portion of patient 24.

The air bladders 122 are then stabilized by evacuating the air from air bladders 122 and using the bead bag position stabilizer 124 to stiffen (or "freeze") the mattress 38 in the desired position. Finally, the temperature of mattress 38 can be adjusted using controller 16, 19, and/or 219 so that control apparatus 86 supplies the necessary signal to thermal pad 126 to change the temperature of thermal pad 126. For example, when thermal pad 126 is a conductive material (such as Gorix™), control apparatus 86 supplies a voltage signal to thermal pad 126 to change the temperature of thermal pad 126.

Another embodiment of the present invention is illustrated in FIGS. 23–25. Surgical table 310 includes a base 312, a pedestal 314 having a bottom end coupled to the base 312, and a support frame 316 coupled to a top end of pedestal 314. Frame 316 includes a head frame section 318, an upper back frame section 320, a lower back frame section 322, a seat frame section 324, and a leg frame section 326. Deck sections 328, 330, 332, 334, and 336 form an articulatable patient support deck 327 extending between frame members 318, 320, 322, 324, and 326, respectively. Mattress 338 is positioned above the deck 327. In the illustrated embodiment, mattress 338 includes head section 340, a torso section 342, and a leg section 344. Each of the sections 340, 342, and 344 of mattress 338 may include a plurality of separate zones. It is understood that mattress 338 may include a different number of separate sections.

A power pack 350 is pivotably mounted to back frame section 320 as best shown in FIG. 25. The power pack 350 includes an outer enclosure or housing 352 which is pivotably coupled to frame section 320 by a suitable connector 353 so that the housing 352 pivots about axis 354. An air coupling 356 is coupled to mattress 338 to supply air to zones or sections 340, 342 and 344 of mattress 338. Air coupling 356 is configured to be inserted into receptacle or aperture 358 so that air is supplied from the power pack 352 through the pivot connector 353 and through the air coupling 356 to the mattress 338. Illustratively, a check valve is located in receptacle 358.

Illustratively, power pack 350 includes an air supply 360 such as a blower or compressor and a plurality of valves 362 for controlling flow of air or other fluid to various zones within the air mattress 338. It is understood that power pack 350 may further include sensors for measuring pressure within the various zones of air mattress 338 and also provide an electrical connection to the air mattress 338, if desired. Electrical connection to the power pack 350 is made by a cable which extends along the frame 316 and through pedestal 314 and base 312. In other embodiments, a power plug may extend directly away from power pack 350 or the power pack 350 may be operated by an internal battery power supply.

When the mattress 338 is located on the deck 327 as shown in FIG. 24, air is supplied from air supply 360 to the zones of mattress 338 from the power pack 350. Deck panels 328, 330, 332, 334, and 336 are illustratively radiolucent so that radiologic procedures can be performed on a patient located on the mattress 338. Power pack 350 is pivotable at least 180° relative to the frame 316 to the position shown in FIG. 24 and shown in dotted lines in FIG. 25 so that region 364 below deck section 330 is free from obstruction during the radiologic procedure or other procedure requiring access to region 364.

It is understood that a plurality of air couplers 356 may be provided to connect different zones of the air mattress 338 to the power pack 350. It is further understood that the power pack 350 may be coupled to other sections of frame 316 on either side of the surgical table 310.

Another embodiment of the present invention is illustrated in FIG. 26. In the FIG. 26 embodiment, an air coupling receptacle 370 is illustratively coupled to the seat deck section 334. A check valve is located in the receptacle. A power pack 372 is pivotably coupled to base 312. In the illustrated embodiment, power pack 372 includes a housing 376 for receiving the air supply, valves, sensors, and/or other electrical components. A pair of spaced apart arms 378 of housing 376 are pivotably coupled to spaced apart side walls 374 of base 312 by pivot connections 380. Power pack 372 is therefore pivotable from an upwardly pivoted position shown in solid lines in FIG. 26 to a downwardly pivoted position shown in dotted lines. In the upwardly pivoted position, the housing 376 is situated over a top surface 382 of base 312 within a footprint of the base 312. Power pack 372 is pivotable in the direction of arrow 384 through a range of motion of about 180° to provide clearance for a C-arm imaging machine or other equipment between the frame 316 and base 312.

Illustratively, the power pack 372 is coupled to a head end of the base 312. It is understood that the power pack 372 may also be coupled to the foot end 386 of base 312 or to side portions of the base 312. Power pack 372 is, therefore, integrated with base 312 but pivotable to permit additional access between the base 312 and the frame 316. Air and electrical lines are illustratively routed through a flexible connector line 388 which extends between the power pack 372 and the base 312. In the illustrated embodiment, the air and electrical lines then run upwardly through pedestal 314 to connector 370. It is understood that air and electrical lines may also run outside the pedestal 314.

Figure 27:
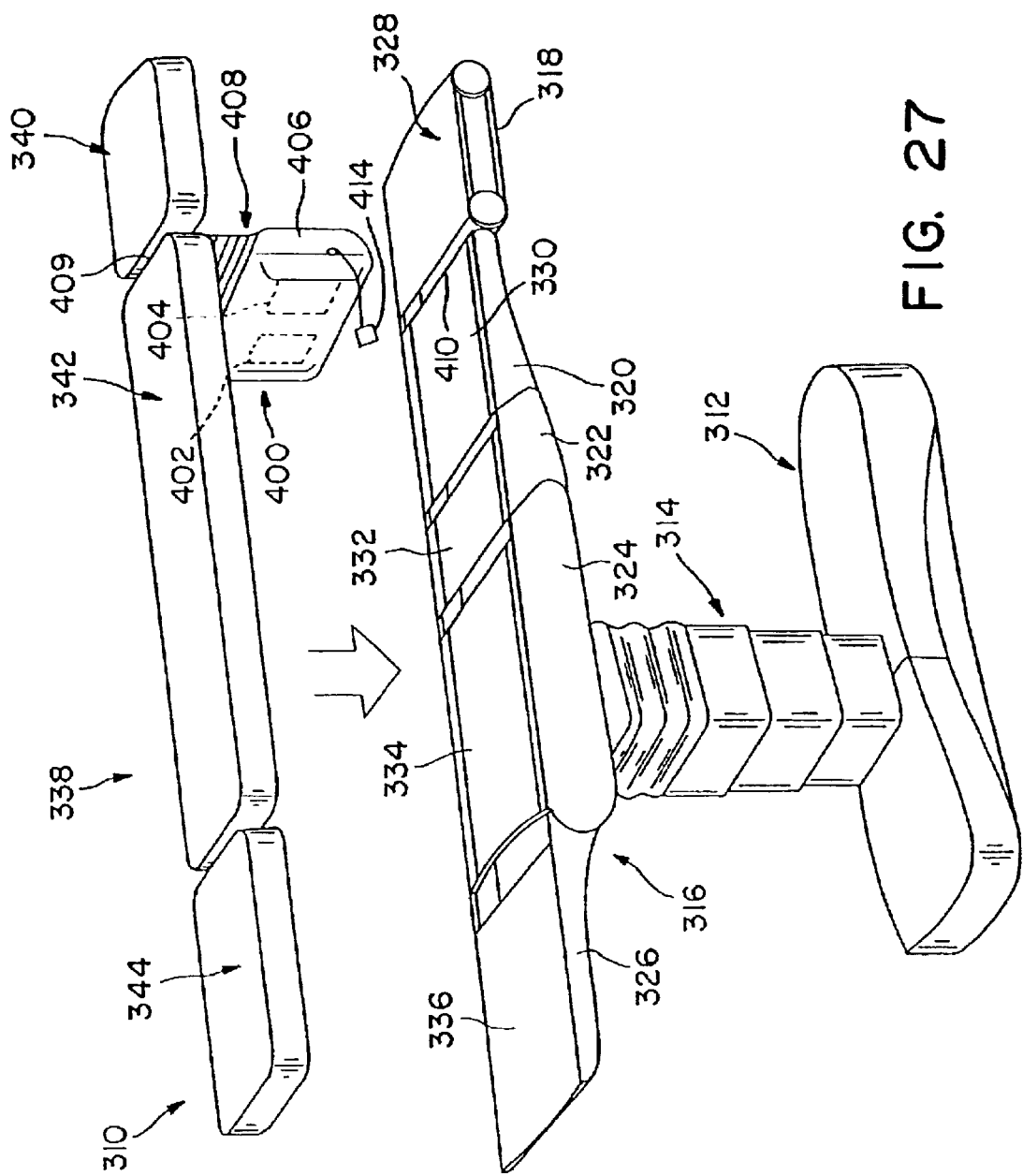
FIG. 27 is an exploded perspective view of yet another embodiment of the present invention illustrating a power pack including an air supply and valves located within an enclosure pivotably coupled to the air mattress.
Figure 28:
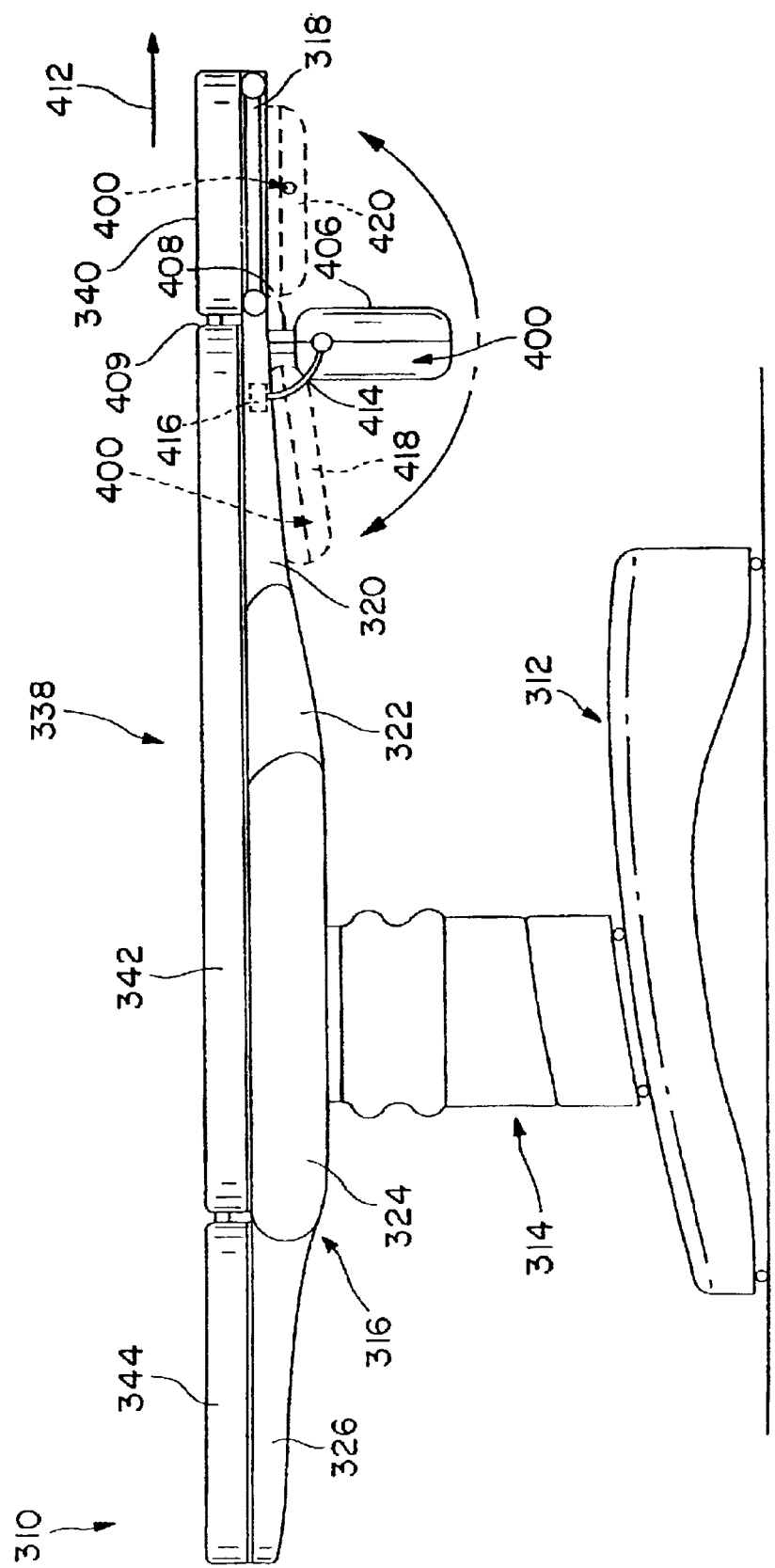
FIG. 28 is a side elevational view of the embodiment of FIG. 27 illustrating positioning of the power pack below the support frame and deck of the surgical table.

Yet another embodiment of the present invention is illustrated in FIGS. 27 and 28. Those elements referenced by numbers identical to FIGS. 23–26 perform the same or similar function. In the embodiment of FIGS. 27 and 28, a power pack 400 is coupled to mattress 338. Power pack 400 includes an air supply 402 and a plurality of valves 404 for supplying air or other fluid to zones of mattress 334. In the illustrated embodiment, the power pack 400 is located within an enclosure or housing 406 which is tethered to an edge 409 of back or torso section 342. Illustratively, enclosure 406 is formed by the same material as the outer cover of mattress 338.

A plurality of air lines pass through the tethered connector 408 to various zones of the mattress 338. In the illustrated embodiment, tethered connector 408 extends downwardly through a slot 410 formed between head deck section 328 and upper back deck section 330 as best shown in FIG. 28. Head frame section 318 is movable outwardly in the direction of arrow 412 in FIG. 28 to permit installation of the mattress 338 and power pack 400. A power connector 414 for the power pack 400 illustratively plugs into a receptacle 416 coupled to frame 316. Illustratively, power is supplied through a power line running from base 312 upwardly through pedestal 314 and along frame 316 to receptacle 416.

The power pack 400 is pivotable upwardly to first and second positions illustrated by dotted line positions 418 and 420. In the dotted line position 418, the power pack 400 is coupled to upper back frame section 320 or deck section 330. In the dotted position 420, power pack 400 is coupled to head frame section 318 or head deck section 328. Power pack 400 is coupled to the frame 316 or deck 327 by suitable fasteners such as Velcro® fasteners, ties, straps, snaps, latches or the like.

In the tucked or upwardly pivoted positions shown in dotted lines 418 and 420, additional room is provided for manipulation of imaging equipment or other equipment below the frame 316. During normal operation, power pack 400 is left in the downwardly hanging position shown in FIG. 27 and in solid lines in FIG. 28 to isolate noise and vibration from the patient.

Although the invention has been described in detail with reference to certain illustrated embodiments, variations and modifications exist within the scope and spirit of the present invention as defined by the following claims.

What is claimed is:

1. A support apparatus, the support apparatus comprising:
   a base,
   a frame coupled to the base,
   a mattress supported by the frame, and
   a power pack coupled to one of the base, the frame and the mattress by a connector located substantially underneath the frame, the power pack being pivotable with respect to the one of the base, the frame, and the mattress between a first area at least partially underneath the frame and a second area substantially outside the first area.

2. The apparatus of claim 1, wherein the first area is located between the frame and the base.

3. The apparatus of claim 1, wherein the frame includes a first
   frame section and a second frame section, the first area is located substantially underneath the first frame section, and the second area is located substantially underneath the second frame section.

4. The apparatus of claim 1, wherein the first area is located substantially within a footprint of the base.

5. The apparatus of claim 1, wherein the second area is located substantially outside the frame.

6. The apparatus of claim 1, wherein the first area is located substantially underneath the frame.

7. A support apparatus comprising:
   a base,
   a frame coupled to the base and adaptable for supporting a mattress in a plurality of positions, and
   means for coupling a power pack to one of a base, a frame and a mattress so that the power pack is pivotable between a first area located at least partially underneath the frame and a second area located substantially outside the first area, the means for coupling being located substantially underneath the frame.

8. The apparatus of claim 7, wherein the means for coupling includes means for supplying a medium to the mattress.

9. The apparatus of claim 8, wherein the medium is one of air and fluid.

10. The apparatus of claim 8, wherein the means for supplying includes means for changing a temperature of the medium.

11. The apparatus of claim 7, wherein the means for coupling extends downwardly below the frame.

12. The apparatus of claim 7, wherein the first area is substantially within a footprint of the base.

13. The apparatus of claim 7, wherein the first area is located between the frame and the base.

14. The apparatus of claim 7, wherein the frame includes a first frame section and a second frame section, the first area is located substantially underneath the first frame section, and the second area is located substantially underneath the second frame section.

15. The apparatus of claim 7, wherein the second area is located substantially outside the frame.

16. The apparatus of claim 7, wherein the first area is located substantially underneath the frame.

17. An apparatus adaptable for supporting a patient in a plurality of positions, the apparatus comprising:
   a base,
   a frame coupled to the base,
   a mattress positioned above the frame, and
   means for coupling a power pack to one of the base, the frame and the mattress so that the power pack is movable between a concealed position and an unconcealed position with respect to the one of the base, the frame and the mattress, the means for coupling being located substantially underneath the frame.

18. The apparatus of claim 17, wherein the concealed position is located substantially underneath the frame.

19. The apparatus of claim 17, wherein the concealed position is located substantially within a footprint of the base.

20. The apparatus of claim 17, wherein the unconcealed position is located at least partially outside the frame.

21. The apparatus of claim 17, wherein the concealed position is located between the frame and the base.

* * * * *